US011154543B2

(12) United States Patent
Guo et al.

(10) Patent No.: US 11,154,543 B2
(45) Date of Patent: Oct. 26, 2021

(54) P38 MAP KINASE INHIBITORS FOR WOUND HEALING

(71) Applicant: The Schepens Eye Research Institute, Inc., Boston, MA (US)

(72) Inventors: Xiaoqing Guo, North Andover, MA (US); James D. Zieske, Wilmington, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 15/768,483

(22) PCT Filed: Oct. 17, 2016

(86) PCT No.: PCT/US2016/057337
§ 371 (c)(1),
(2) Date: Apr. 13, 2018

(87) PCT Pub. No.: WO2017/066758
PCT Pub. Date: Apr. 20, 2017

(65) Prior Publication Data
US 2018/0296546 A1 Oct. 18, 2018

Related U.S. Application Data

(60) Provisional application No. 62/242,148, filed on Oct. 15, 2015.

(51) Int. Cl.
| | | |
|---|---|---|
| *A61K 31/4439* | (2006.01) |
| *A61K 9/00* | (2006.01) |
| *A61K 31/506* | (2006.01) |
| *A61K 31/44* | (2006.01) |
| *A61K 31/496* | (2006.01) |
| *A61K 31/416* | (2006.01) |
| *A61K 31/5355* | (2006.01) |
| *A61K 31/519* | (2006.01) |
| *A61P 27/02* | (2006.01) |
| *A61P 17/00* | (2006.01) |
| *A61K 31/5377* | (2006.01) |

(52) U.S. Cl.
CPC ........ *A61K 31/4439* (2013.01); *A61K 9/0048* (2013.01); *A61K 31/416* (2013.01); *A61K 31/44* (2013.01); *A61K 31/496* (2013.01); *A61K 31/506* (2013.01); *A61K 31/519* (2013.01); *A61K 31/5355* (2013.01); *A61K 31/5377* (2013.01); *A61P 17/00* (2018.01); *A61P 27/02* (2018.01)

(58) Field of Classification Search
None
See application file for complete search history.

(56) References Cited

U.S. PATENT DOCUMENTS

| | | |
|---|---|---|
| 2006/0189541 A1 | 8/2006 | Gamache |
| 2006/0234911 A1* | 10/2006 | Hoffmann .......... A61K 38/1875 514/183 |
| 2012/0276064 A1 | 11/2012 | Blau et al. |
| 2014/0235637 A1 | 8/2014 | Kossen et al. |
| 2015/0044178 A1 | 2/2015 | Kinoshita et al. |

FOREIGN PATENT DOCUMENTS

WO WO-2015/072580 A1 5/2015

OTHER PUBLICATIONS

Underwood et al., American Journal of Physiology, Lung, Cellular and Molecular Physiology (2000), 279)5), pp. L895-L902.*
Nassar et al., Journal of Glaucoma (Feb. 2015), 24(2), pp. 165-178.*
Prakash et al., The Journal of Pharmacology and Experimental Therapeutics (2006), 319(1), pp. 8-19.*
Szuster-Ciesielska et al., Journal of Gastroenterology (2013), 48(2), pp. 222-237.*
Kalluri et al., The Journal of Clinical Investigation (2003), 112(12), pp. 1776-1784.*
Adams et al. (Sep. 1, 1993) "Highly Specific in Vivo Tumor Targeting by Monovalent and Divalent Forms of 741F8 Anti-c-erbB-2 Single-Chain Fv", Cancer Research, 53:4026-4034.
Gruber et al. (Jun. 1, 1994) "Efficient tumor cell lysis mediated by a bispecific single chain antibody expressed in *Escherichia coli*", The Journal of Immunology, 152(11):5368-5374.
Guo et al. (Sep. 2007) "Morphologic Characterization of Organized Extracellular Matrix Deposition by Ascorbic Acid-Stimulated Human Corneal Fibroblasts", Investigative Ophthalmology & Visual Science, 48(9):4050-4060.
Hollinger et al. (Jul. 1993) "Diabodies: Small Bivalent and Bispecific Antibody Fragments", PNAS, 90:6444-6448.
Hu et al. (Jul. 1, 1996) "Minibody: A Novel Engineered Anti-Carcinoembryonic Antigen Antibody Fragment (Single-Chain Fv-CH3) Which Exhibits Rapid, High-Level Targeting of Xenografts", Cancer Research, 56:3055-3061.
Kostelny et al. (Mar. 1, 1992) "Formation of a Bispecific Antibody by the Use of Leucine Zippers", Journal of Immunology, 148(5):1547-1553.
McCafferty et al. (Dec. 6, 1990) "Phage Antibodies: Filamentous Phage Displaying Antibody Variable Domains", Nature, 348(6301):552-554.
McCartney et al. (Mar. 1995) "Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides", Protein Engineering, 8(3):301-314.
Pack et al. (1992) "Miniantibodies: use of amphipathic helices to produce functional, flexibly linked dimeric FV fragments with high avidity in *Escherichia coli*", Biochemistry, 31(6):1579-1584.

(Continued)

*Primary Examiner* — Brian J Davis
(74) *Attorney, Agent, or Firm* — Fish & Richardson P.C.

(57) ABSTRACT

Methods of the invention treat, reduce, or reverse fibrosis of a bodily tissue by administering to the local affected tissue a composition comprising an inhibitor of p38 MAP kinase, which treatment leads to a reduction or reversal of fibrosis.

26 Claims, 7 Drawing Sheets

Specification includes a Sequence Listing.

(56) References Cited

OTHER PUBLICATIONS

Zhu et al. (1997) "Remodeling domain interfaces to enhance heterodimer formation", Protein Science, 6:781-788.
Chung et al., "Synchronization of the G1/S Transition in Response to Corneal Debridement," IOVS, Aug. 1999; 40(9):1952-1958.
PCT International Preliminary Report on Patentability in International Appln. No. PCT/US2016/057337, dated Apr. 26, 2018, 8 pages.
PCT International Search Report and Written Opinion in International Appln. No. PCT/US2016/057337, dated Jan. 17, 2017, 10 pages.

* cited by examiner

A

B

P38 MAP KINASE INHIBITORS FOR WOUND HEALING

CROSS-REFERENCES TO RELATED APPLICATIONS

This application is a national stage application filed under 35 U.S.C. § 371, of International Patent Application No. PCT/US2016/057337, filed Oct. 17, 2016, which claims the benefit of and priority under 35 U.S.C. § 119(e) to U.S. Provisional Application No. 62/242,148, filed Oct. 15, 2015, the entire contents of each of which are hereby expressly incorporated by reference herein.

STATEMENT AS TO FEDERALLY SPONSORED RESEARCH

This invention was made with government support under R01-EY005665 awarded by the National Institutes of Health. The government has certain rights in the invention.

INCORPORATION BY REFERENCE OF SEQUENCE LISTING

The contents of the txt file named 36770-549001WO_ST25.TXT, created on Oct. 14, 2016, and is 12,975 bytes in size, are hereby incorporated by reference in their entireties.

FIELD OF THE INVENTION

The present invention relates to compositions and methods for the treatment and prevention of scar tissue.

BACKGROUND OF THE INVENTION

Fibrosis, or scarring, can occur after trauma of a bodily tissue and as an end result of a variety of diseases. It allows for a tissue to rapidly repair itself, however, it results in a less than optimal tissue that can be rigid and lacking tensile strength. In the cornea, fibrosis results in an opaque cornea that can interfere with and even cause loss of vision. Scarring is most commonly stimulated by the activation and release of transforming growth factor-beta (TGF-β). This growth factor stimulates the differentiation of the normally quiescent cells in the tissue to take on a contractile phenotype called myofibroblasts. These cells are associated with scarring and can be identified by the presence of α-smooth muscle actin (αSMA or SMA). TGF-β functions by binding to a cell surface receptor that activates several signaling pathways.

Fibrosis of organs is an irreversible progressive change arising due to acute or chronic inflammatory conditions leading to excess deposition of extracellular matrix. This leads to loss of normal architecture and function of the organ that can lead to organ failure. Chronic loss of organ function in most organs, including bone marrow, heart, intestine, kidney, liver, lung, and skin, is associated with fibrosis contributing to an estimated one third of natural deaths worldwide. Fibrosis in the eye, while not fatal, can be vision threatening and, in extreme cases, blinding. Effective therapies to treat, prevent or reverse existing fibrotic lesions are not yet available in any organ.

At present, there is no known treatment for conical scarring. Vitamin E, rosehip oil and various growth factors are sometimes suggested for the prevention of scarring at the time of wound healing with minimal efficacy. These minimally effective therapies are utilized immediately following injury in hopes to alleviate scar tissue deposition during healing. Due to the potentially debilitating effects of scarring in the cornea there is a need for an effective therapy for the treatment or prevention of such scarring and a therapy that can be administered prior to, immediately following an injurious event, or once wound healing and subsequent scarring has already occurred. The present invention provides compositions and methods acting at the underlying fibrosis pathways that function as antifibrotic therapies that are effective in ocular and other tissues.

SUMMARY OF THE INVENTION

The term fibrosis describes the development of fibrous connective tissue as a reparative response to injury or damage. Fibrosis may refer to the connective tissue deposition that occurs as part of normal healing or to the excess tissue deposition that occurs as a pathological process. Thus, fibrosis includes the thickening and scarring of connective tissue, usually as a result of injury. Scarring and thickening of the tissue can impede or reduce the normal functioning of the affected tissue. The methods and compositions described herein inhibit the formation of scar tissue or fibrosis. Surprisingly, the methods and compositions reverse fibrosis, e.g., reduce the thickness and/or stiffness (rigidity) of pre-existing or developing scar tissue.

The invention provides methods with a significant advantage over previous methods for wound healing and an important advancement in the field of scar tissue formation, because it preserves the beneficial aspects of healing, while blocking or inhibiting the detrimental action of αSMA that leads to scarring. The methods allow beneficial wound healing to proceed while scar tissue formation is inhibited. Prior to the invention, approaches to conical scars included (a) taking no action, or (b) corneal transplant; similarly for dermal scarring, approaches included (a) taking no action, or (b) performing a second surgery to reduce the scar.

Described herein are methods and compositions for the treatment and prevention of tissue scarring such as corneal and dermal scarring. Inhibitors for one or more members of p38 MAP kinase (also referred herein as "p38") signaling pathway (e.g., p38 MAP kinase) block the induction of αSMA that follows TGF-β activation following cellular injury. For example, a compound or composition selectively inhibits the activity of one or more p38 isoforms (e.g., p38α, p38β, p38γ and/or p38δ). Selective inhibitors reduce the activity of p38 by a greater amount compared to the reduction of other MAP kinases. For example, the selective inhibitors reduce p38 activity by at least 10%, 25%, 50%, 75%, 2-fold, 5-fold, 10-fold, or more compared to the inhibition of other MAP kinases. This reduction of p38 activity in cells leads to a reduction in scar tissue deposition (formation of a new scar) as well as a change from pre-existing to non-scar tissue after treatment. Other participants in the p38 signal transduction pathway are optionally inhibited or blocked alone or in conjunction with p38 inhibition for the purpose of treating or reducing fibrosis. αSMA is responsible for the induction of myofibroblasts to a wound site resulting in scarring. Scarring in the cornea can negatively affect vision, causing visual haze, or even causing blindness. Other disorders or diseases associated with tissue scarring or fibrosis include scarring of skin, heart, lung, or kidney tissue.

A method of the present invention for treating or reducing fibrosis of a bodily tissue, includes administering to the local affected bodily tissue a composition comprising an inhibitor of p38 MAP kinase. For example, the p38 inhibitors reduce deposition of and/or reduce scar tissue thickness or stiffness (in pre-existing scars) by at least 10%, 25%, 50%, 75%, 2-fold, 5-fold, 10-fold, or more.

The method may include compositions comprising a small molecule inhibitor of p38 MAP kinase or an antibody inhibitor of p38 MAP kinase. The inhibitor of p38 MAP kinase is not or does not comprise an inhibitor of SMAD proteins. Small molecule inhibitors of p38 MAP kinase may include SB 203580, SB 239063, SB 220025, SB 242235, BIRB-796, VX-702, VX-745, AMG-548, ARRY-797, PH 797804, ARRY-614, SB 681323; GW 856553, SC10-469, BMS 582949, RO 4402257, CNI-1493, or SB202190.

Compositions of the invention may be administered following injury to the cornea or skin tissue. Administration may be within 24 hours following injury to the cornea or skin tissue. Alternatively, the compositions of the invention may be administered locally in advance of a surgical procedure and/or during surgery, and/or subsequent to surgery (even after scar tissue formation has occurred).

The compositions of the invention may be in an aqueous or oil-based solution or an emulsion. The compositions of the invention may be in the form of an eye drop, a cream, or an ointment. The compositions may be administered topically. The compositions of the invention may further include small molecule, antibody, peptide, or nucleotide therapeutic inhibitors of p38 MAP kinase. The inhibitor of p38 MAP kinase may be present in the composition in a concentration of 0.10% to 5.0% (w/v). The composition may further include pharmaceutically acceptable excipients, fillers, or solvents. The compositions of the invention may not comprise an inhibitor of SMAD proteins.

Further provided herein is a method for reducing fibrosis of the cornea or skin. The method includes the steps of: identifying a subject with fibrosis in a skin or corneal tissue; and locally administering to the skin or corneal tissue a topical composition comprising an inhibitor of p38 MAP kinase. Compositions used in the methods of the invention may be in the form of an eye drop, a cream, or an ointment.

Also within the invention is a composition for treating, reducing, or reversing fibrosis of a bodily tissue, comprising: administering to local affected tissue, e.g., site of injury or site of a pre-existing scar, a composition comprising an inhibitor of a factor of p38 MAP kinase signaling pathway, thereby treating, reducing, or reversing fibrosis.

The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb. The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. Percent identity is determined using methods known in the art, e.g., Clustal W or Clustal Omega (clustal.org/omega).

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a siRNA, (e.g., shRNA, miRNA, snoRNA), compound or small molecule, an antibody or a fragment thereof, a polypeptide, or a nucleic acid therapeutic that inhibits cellular function (e.g., p38 signaling transduction) e.g., by binding, partially or totally blocking stimulation, decrease, prevent, or delay activation, or inactivate, desensitize, or down-regulate signal transduction, gene expression or enzymatic activity necessary for protein activity. A "p38 inhibitor" refers to a substance that results in a detectably lower expression of genes or proteins or lower activity level of p38 as compared to those levels without such substance. As used herein, the term "selective p38 inhibitor" or "a composition that selectively inhibits p38" denotes a natural or synthetic compound (e.g., a small molecule, a polypeptide, a polynucleotide, an antibody or a fragment thereof) which is characterized by inhibitory activity of p38 that is considerably greater than the inhibitory activity for other members of the MAP kinase family.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "VH," or "VH" refer to the variable region of an immunoglobulin heavy chain, including an Fv, scFv, dsFv or Fab; while the terms "variable light chain," "VL" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., Fundamental Immunology (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) Nature 348:552). The term "antibody" also includes bivalent or bispecific molecules, diabodies, triabodies, and tetrabodies. Bivalent and bispecific molecules are described in, e.g., Kostelny et al. (1992) J. Immunol. 148:1547, Pack and Pluckthun (1992) Biochemistry 31:1579, Hollinger et al. (1993), PNAS. USA 90:6444, Gruber et al. (1994) J Immunol. 152:5368, Zhu et al. (1997) Protein Sci. 6:781, Hu et al. (1996) Cancer Res. 56:3055, Adams et al. (1993) Cancer Res. 53:4026, and McCartney, et al. (1995) Protein Eng. 8:301.

A "pharmaceutical composition" is a formulation containing the nucleic acids described herein in a form suitable for administration to a subject. In embodiments, the pharmaceutical composition is in bulk or in unit dosage form. The unit dosage form is any of a variety of forms, including, for example, a syringe volume or other filled dispenser, a capsule, an IV bag, a tablet, a single pump on an aerosol inhaler or a vial. The quantity of active ingredient (e.g., a formulation of the disclosed nucleic acid) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including topical, implantation of sustained release devices such as nanowafer drug delivery systems, oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions and patches. In embodiments, the active nucleic acid is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. A thorough discussion of pharmaceutically acceptable excipients is available in REMINGTON'S PHARMACEUTICAL SCIENCES (Mack Pub. Co., N.J. 1991). Pharmaceutically acceptable excipients in therapeutic compositions may contain liquids such as water, saline, glycerol and ethanol. Additionally, auxiliary substances, such as wetting or emulsifying agents, pH buffering substances, and the like, may be present in such vehicles. A pharmaceutical formulation may include an active pharmaceutical ingredient and one or more excipients (pharmaceutically inactive ingredient).

The terms "subject," "individual," and "patient" are used interchangeably herein to refer to a vertebrate, preferably a mammal, more preferably a human. The mammal can be e.g., a human or appropriate non-human mammal, such as primate, mouse, rat, dog, cat, cow, horse, goat, camel, sheep or a pig. The subject can also be a bird or fowl. Tissues, cells and their progeny of a biological entity obtained in vivo or cultured in vitro are also encompassed. As used herein, a "subject in need thereof" or "a patient" may be a subject having a fibrosis.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated (e.g., fibrosis). Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, contents of GENBANK Accession citations, and other publications cited herein are hereby incorporated by reference in their entirety for all purposes.

BRIEF DESCRIPTION OF THE DRAWINGS

FIG. 2A shows corneal fibroblasts cultured with Basic Medium (BM: Eagles minimum essential medium) for 48 hours. FIG. 2B shows corneal fibroblasts cultured with BM for 24 hours, then BM+TGF-β1 for 24 hours, FIG. 2C shows corneal fibroblasts cultured with BM for 24 hours, then BM+p38 inhibitor for 24 hours. FIG. 2D shows corneal fibroblasts cultured with BM+p38 Inhibitor for 24 hours, then BM+p38 inhibitor+TGF-β1. Grey stripes staining=SMA and grey dots staining=DAPI, a nuclear counterstain. The number of SMA-positive cells was quantitated and FIG. 2B is significantly different (p<0.0001) than the other three samples. This is in agreement with the western blot in FIG. 1.

DETAILED DESCRIPTION

The pathway most commonly associated with TGF-β signaling involves the SMAD proteins; however, when utilizing a SMAD inhibitor produces no effect on the generation of SMA expressing myofibroblasts. SMADs are intracellular proteins that transduce extracellular signals from transforming growth factor beta ligands to the nucleus where they activate downstream gene transcription. The SMAD proteins are homologs of both the *Drosophila* protein, mothers against decapentaplegic (MAD) and the *Caenorhabditis elegans* protein SMA (from gene sma for small body size); the nomenclature of SMAD proteins is a blending of the two. The term SMAD is a contraction of Sma and Mad (Mothers against decapentaplegic).

Figures 2A, 2B, 2C, 2D:
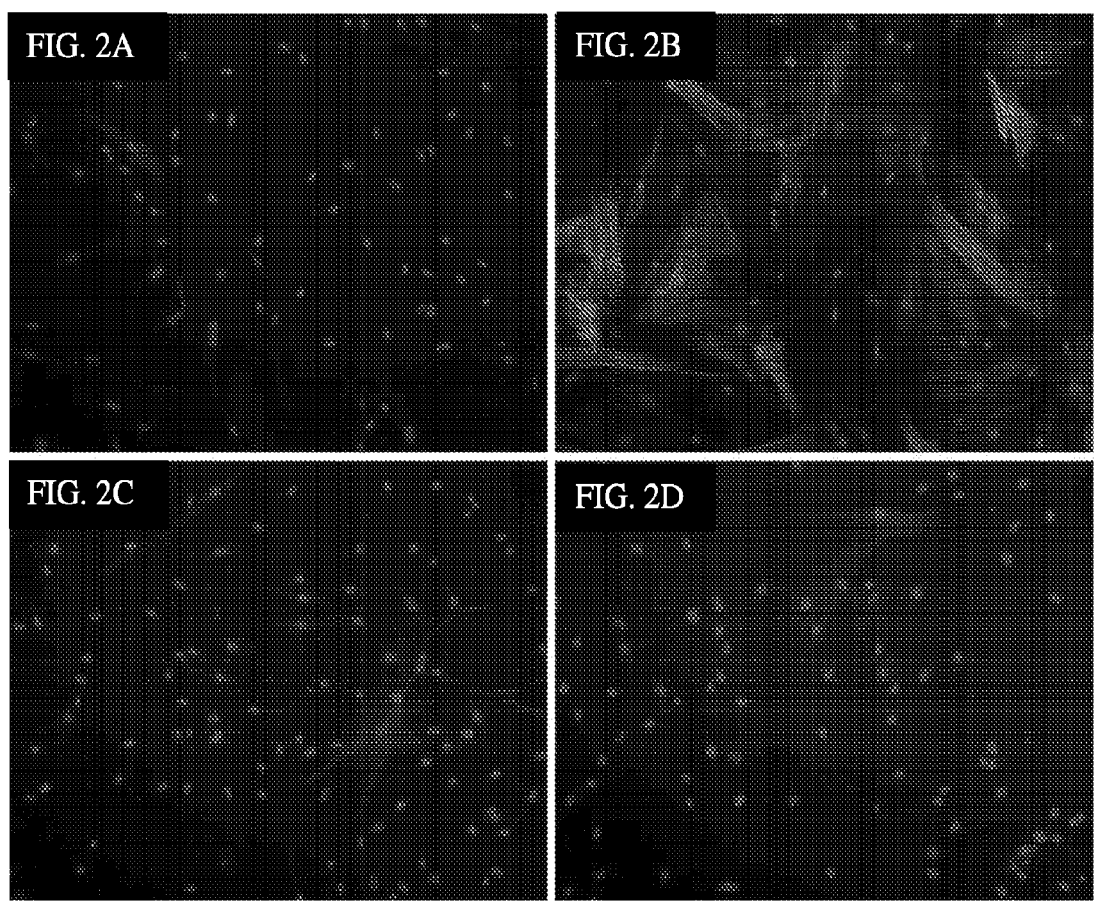
FIGS. 2A-2D are representative indirect immunofluorescent images of human corneal fibroblasts. Each image shows a corneal fibroblast in different culture conditions.
Figure 3:
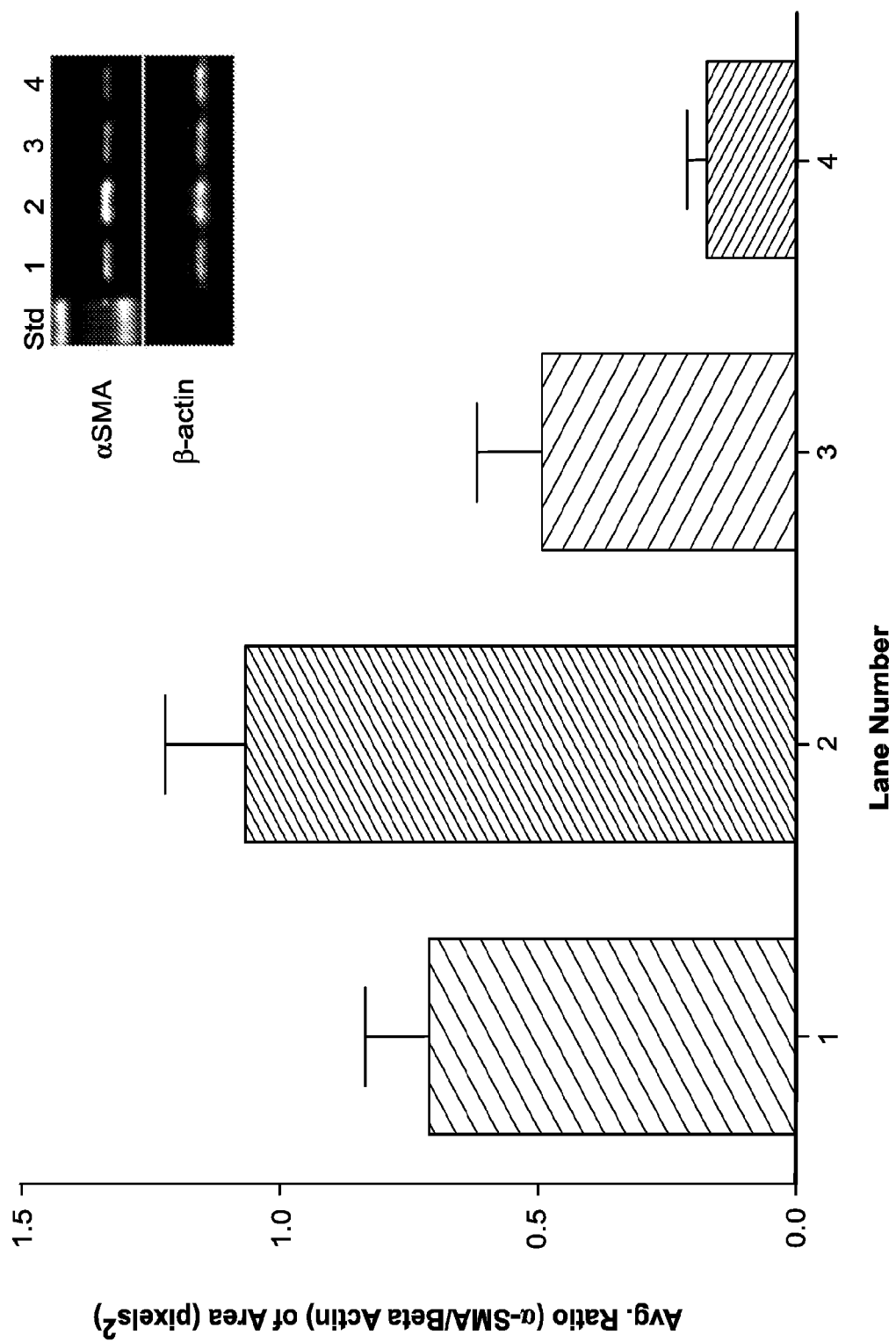
FIG. 3 is an image of a representative western blot of human dermal fibroblasts cultured with 1) Basic Medium (BM: Eagles minimum essential medium)+10% FBS for 48 hours; 2) BM+10% FBS for 24 hours, then BM+10% FBS+TGFβ1 for 24 hours, 3) BM+10% FBS for 24 hours, then BM+10% FBS+p38 inhibitor for 24 hours, and 4) BM+10% FBS+p38 Inhibitor for 24 hours, then BM+10% FBS+p38 inhibitor+TGF-β1. Graph of SMA corrected per lane with internal control (β-actin). Lane 2 is significantly different (p<0.05 and p<0.01) than the lanes 3 and 4, respectively.

Subsequently, it was discovered that p38map kinase inhibitor almost completely blocked SMA expression in both human corneal fibroblasts (FIGS. 1-2) and human dermal fibroblasts (FIG. 3). The data on the dermal fibroblasts is even more provocative, as the dermal cells in our culture system have already differentiated into myofibroblasts, indicating that inhibition of the p38 pathway reverses the myofibroblast phenotype.

The blockage of the p38 pathway can be used to treat corneal and dermal scarring. Since both of these tissues are readily accessible, the p38 inhibitor is applied by means of an eye drop, cream, or ointment.

Wound Healing Pathway

Wound healing as it pertains to the present invention can encompass any epithelial layer including wounding to the dermal epithelium or cornea. Corneal injury may arise from different mechanisms, including disorders such as aging or tear deficiency, or injury caused by microorganisms, chemicals, or mechanical damage, e.g. laser surgery. Injury triggers the release of growth factors and cytokines as described below.

Wound healing progresses via 3 overlapping phases: inflammation, granulation, and tissue remodeling. After cutaneous injury, a blood clot forms, and inflammatory cells infiltrate the wound, secreting cytokines and growth factors to initiate the inflammation phase. During the granulation phase, fibroblasts and other cells differentiate into myofibroblasts, which deposit extracellular matrix (ECM) proteins. Simultaneously, angiogenesis occurs, and keratinocytes proliferate and migrate to close the wound. In the final tissue remodeling phase, apoptosis eliminates myofibroblasts and extraneous blood vessels, and the ECM is remodeled to resemble the original tissue. Fibrosis occurs when inappropriate tissue remodeling results in excess ECM deposition due to myofibroblast survival or lack of ECM proteolytic degradation. At the other extreme of wound healing pathophysiology, chronic wounds feature dysregulated tissue remodeling with enhanced ECM degradation. As wound healing and its dysregulation via fibrosis and other means occur in all tissues, analysis of these mechanisms may yield novel drug targets for a variety of disorders.

In corneal wound healing two paracrine growth factors, hepatocyte growth factor (HGF) and keratinocyte growth factor (KGF), induced rapid and marked activation and prompt nuclear accumulation of phospho-p38 (p-p38) and -ERK1/2 (p-ERK1/2), but not of JNK (p-JNK1/2). Furthermore, TGF-β receptors type I and II are upregulated after wounding. The Smad proteins, including Smad2 and 3 translocate into the nucleus after activation via the TGF-β receptors. The Smad pathway is the most understood TGF-β pathway and is initiated by the phosphorylation and activation of Smad2 and 3, TGF-β-specific intracellular signal transducers. The phosphorylated Smad2 and 3 interact with the common Smad (Smad4) and form heterodimeric and heterotrimeric complexes. These complexes then translocate into the nucleus and bind to transcription factors, coactivators, or corepressors, to activate or inhibit the expression of TGF-β-response genes.

SARA (Smad anchor for receptor activation) was identified in 1998 as a Smad2 and 3 interacting protein. After TGF-β stimulation, SARA recruits Smad2 or 3 to the TGFβRI portion of the RII/I complex. Once recruited, the Smad2 or 3 is phosphorylated, released from SARA and assembled into Smad2/4 and Smad3/4 complexes. Trx-SARA is comprised of a rigid scaffold Trx (the *Escherichia coli* thioredoxin A protein) followed by Smad-binding domain of SARA (a constrained 56-amino acid Smad-binding motif from the SARA protein). By binding to monomeric Smad proteins, Trx-SARA reduces the level of Smad2 and 3 in complex with Smad4 after TGF-β stimulation. It has been demonstrated that Trx-SARA is an effective inhibitor of the Smad pathway, and a useful tool for studying activation of different proteins in TGF-β signaling pathways. Data described herein show that blocking Smad signaling pathway does not change the αSMA protein expression in HCF. This suggests that SMA expression is not regulated through the SMAD pathway, but rather through a pathway involving p38.

The term "p38 MAP kinase" or "p38" refers to a class of mitogen-activated protein kinases that are responsive to stress stimuli, such as cytokines, ultraviolet irradiation, heat shock, and osmotic shock, and are involved in cell differentiation, apoptosis and autophagy. p38 MAP Kinase (MAPK), also called RK or CSBP (Cytokinin Specific Binding Protein), is the mammalian orthologue of the yeast Hog 1p MAP kinase, which participates in a signaling cascade controlling cellular responses to cytokines and stress. Four p38 MAP kinases, p38-α (MAPK14), -β (MAPK11), -γ (MAPK12/ERK6), and -δ (MAPK13/SAPK4), have been identified. Similar to the SAPK/JNK pathway, p38 MAP kinase is activated by a variety of cellular stresses including osmotic shock, inflammatory cytokines, lipopolysaccharides (LPS), Ultraviolet light, and growth factors. Exemplary p38 inhibitors may associate with or bind to a protein kinase domain (see below) or inhibit the binding of a p38 protein to a ligand required for signal transduction.

The term "p38-α (MAPK14)" as provided herein includes any of the p38-α (MAPK14) protein naturally occurring forms, homologs or variants that maintain the activity of p38-α (MAPK14) (e.g., within at least 50%, 80%, 90%, 95%, 96%, 97%, 98%, 99% or 100% activity compared to the native protein). In embodiments, variants or homologs have at least 50%, 80%, 85%, 90%, 91%, 92%, 93%, 94%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form of SEQ ID NO: 1. In embodiments, p38-α (MAPK14) protein used herein is the protein identified as UniProtKB-Q16539.

```
MSQERPTFYR QELNKTIWEV PERYQNLSPV GSGAYGSVCA

AFDTKTGLRV AVKKLSRPFQ SIIHAKRTYR ELRLLKHMKH

ENVIGLLDVF TPARSLEEFN DVYLVTHLMG ADLNNIVKCQ

KLTDDHVQFL IYQILRGLKY IHSADIIHRD LKPSNLAVNE

DCELKILDFG LARHTDDEMT GYVATRWYRA PEIMLNWMHY

NQTVDIWSVG CIMAELLTGR TLFPGTDHID QLKLILRLVG
```

```
TPGAELLKKI SSESARNYIQ SLTQMPKMNF ANVFIGANPL

AVDLLEKMLV LDSDKRITAA QALAHAYFAQ YHDPDDEPVA

DPYDQSFESR DLLIDEWKSL TYDEVISFVP PPLDQEEMES
```

(SEQ ID NO: 1, underlined indicates the protein kinase domain 24-308 aa)

underlined indicates the protein kinase domain 24-308 aa)

The term "p38-β (MAPK11)" as provided herein includes any of the p38-β (MAPK11) protein naturally occurring forms, homologs or variants that maintain the activity of p38-β (MAPK11) (e.g., within at least 50%, 80%, 90%, 95%, 96%, 97%, 98%, 99% or 100% activity compared to the native protein). In embodiments, variants or homologs have at least 50%, 80%, 85%, 90%, 91%, 92%, 93%, 94%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form of SEQ ID NO: 2. In embodiments, p38-β (MAPK11) protein used herein is the protein identified as UniProtKB-Q15759.

```
MSGPRAGFYR QELNKTVWEV PQRLQGLRPV GSGAYGSVCS

AYDARLRQKV AVKKLSRPFQ SLIHARRTYR ELRLLKHLKH

ENVIGLLDVF TPATSIEDFS EVYLVTTLMG ADLNNIVKCQ

ALSDEHVQFL VYQLLRGLKY IHSAGIIHRD LKPSNVAVNE

DCELRILDFG LARQADEEMT GYVATRWYRA PEIMLNWMHY

NQTVDIWSVG CIMAELLQGK ALFPGSDYID QLKRIMEVVG

TPSPEVLAKI SSEHARTYIQ SLPPMPQKDL SSIFRGANPL

AIDLLGRMLV LDSDQRVSAA EALAHAYFSQ YHDPEDEPEA

EPYDESVEAK ERTLEEWKEL TYQEVLSFKP PEPPKPPGSL

EIEQ
```

(SEQ ID NO: 2, underlined indicates the protein kinase domain 24-308 aa)

The term "p38-γ (MAPK12/ERK6)" as provided herein includes any of the p38-γ (MAPK12/ERK6) protein naturally occurring forms, homologs or variants that maintain the activity of p38-β (MAPK11) (e.g., within at least 50%, 80%, 90%, 95%, 96%, 97%, 98%, 99% or 100% activity compared to the native protein). In embodiments, variants or homologs have at least 50%, 80%, 85%, 90%, 91%, 92%, 93%, 94%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form of SEQ ID NO: 3. In embodiments, p38-γ (MAPK12/ERK6) protein used herein is the protein identified as UniProtKB-P53778.

```
MSSPPPARSG FYRQEVTKTA WEVRAVYRDL QPVGSGAYGA

VCSAVDGRTG AKVAIKKLYR PFQSELFAKR AYRELRLLKH

MRHENVIGLL DVFTPDETLD DFTDFYLVMP FMGTDLGKLM

KHEKLGEDRI QFLVYQMLKG LRYIHAAGII HRDLKPGNLA

VNEDCELKIL DFGLARQADS EMTGYVVTRW YRAPEVILNW
```

-continued

```
MRYTQTVDIW SVGCIMAEMI TGKTLFKGSD HLDQLKEIMK

VTGTPPAEFV QRLQSDEAKN YMKGLPELEK KDFASILTNA

SPLAVNLLEK MLVLDAEQRV TAGEALAHPY FESLHDTEDE

PQVQKYDDSF DDVDRTLDEW KRVTYKEVLS FKPPRQLGAR

VSKETPL (SEQ ID NO: 3, underlined indicates the protein
kinase domain 27-311 aa)
```

The term "p38-δ (MAPK13/SAPK4)" as provided herein includes any of the p38-δ (MAPK13/SAPK4) protein naturally occurring forms, homologs or variants that maintain the activity of p38-δ (MAPK13/SAPK4) (e.g., within at least 50%, 80%, 90%, 95%, 96%, 97%, 98%, 99% or 100% activity compared to the native protein). In embodiments, variants or homologs have at least 50%, 80%, 85%, 90%, 91%, 92%, 93%, 94%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form of SEQ ID NO: 4. In embodiments, p38-δ (MAPK13/SAPK4) protein used herein is the protein identified as UniProtKB-O15264.

```
MSLIRKKGFY KQDVNKTAWE LPKTYVSPTH VGSGAYGSVC

SAIDKRSGEK VAIKKLSRPF QSEIFAKRAY RELLLLKHMQ

HENVIGLLDV FTPASSLRNF YDFYLVMPFM QTDLQKIMGM

EFSEEKIQYL VYQMLKGLKY IHSAGVVHRD LKPGNLAVNE

DCELKILDFG LARHADAEMT GYVVTRWYRA PEVILSWMHY

NQTVDIWSVG CIMAEMLTGK TLFKGKDYLD QLTQILKVTG

VPGTEFVQKL NDKAAKSYIQ SLPQTPRKDF TQLFPRASPQ

AADLLEKMLE LDVDKRLTAA QALTHPFFEP FRDPEEETEA

QQPFDDSLEH EKLTVDEWKQ HIYKEIVNFS PIARKDSRRR

SGMKL (SEQ ID NO: 4, underlined indicates the protein
kinase domain 25-308 aa)
```

The term "factor of p38 signaling pathway" refers to a molecule that functions in p38 signaling pathway. Exemplary factors of p38 signaling pathway include, but are not limited to, MKK3, MKK6, MKK4, TAO1, TAO2, TAO3, DLK, MEKK1, MEEK2, MEEK3, MEEK4, MLK2, MLK3, ASK1, ASK2, TAK1, PAK1, Src, Rac, Ras, CDC42, TAB1, TAB2, MAPKAPK2, MAPKAPK3, MSK1, MSK2, PRAK, CDC26, ATF-2, STAT1, the Max/Myc complex, MEF-2, Elk-1.

Full names of these molecules are: MKK3 (dual specificity mitogen activated protein kinase kinase 3 or MAP kinase kinase 3), MKK6 (dual specificity mitogen activated protein kinase kinase 6 or MAP kinase kinase 6), MKK4 (dual specificity mitogen activated protein kinase kinase 4), TAO1 (Tomato Aldehyde Oxidase 1), TAO2 (Tomato Aldehyde Oxidase 2), TAO3 (Tomato Aldehyde Oxidase 3), DLK (Dual leucine zipper kinase or mitogen-activated protein kinase kinase kinase 12), MEKK1 (mitogen-activated protein kinase kinase kinase 1), MEEK2 (mitogen-activated protein kinase kinase kinase 2 or MAP/ERK kinase kinase 2), MEEK3 (mitogen-activated protein kinase kinase kinase 3 or MAP/ERK kinase kinase 3), MEEK4 (mitogen-activated protein kinase kinase kinase 4), MLK2 (mixed lineage kinase 2), MLK3 (mitogen-activated protein kinase kinase kinase 11 or mixed lineage kinase 3), ASK1 (Apoptosis signal-regulating kinase 1), ASK2 (Apoptosis signal-regulating kinase 2), TAK1 (TGFbeta activated kinase 1), PAK1 (p21 activated kinase 1), Src (V-SRC Avian Sarcoma (Schmidt-Ruppin A-2) Viral Oncogene), Rac (Ras-related C3 botulinum toxin substrate), Ras (retrovirus-associated DNA sequences), CDC42 (cell division control protein 42 homolog), TAB1 (TAK1-binding protein 1 or TGF-beta activated kinase 1/MAP3K7 binding protein 1), TAB2 (TGF-beta activated kinase 1/MAP3K7 binding protein 2), MAPKAPK2 (mitogen-activated protein kinase-activated protein kinase 2), MAPKAPK3 (mitogen-activated protein kinase-activated protein kinase 3), MSK1 (ribosomal protein S6 kinase A5), MSK2 (ribosomal protein S6 kinase A4), PRAK (mitogen-activated protein kinase-activated protein kinase 5), CDC26 (cell division cycle 26), ATF-2 (Activating transcription factor 2), STAT1 (signal transducer and activator of transcription), the Max (myc-associated factor X)/Myc (v-myc avian myelocytomatosis viral oncogene homolog) complex, MEF-2 (myocyte enhancer factor-2), Elk-1 (ETS transcription factor).

P38 Inhibitors

Compositions of the invention include any agent with the ability to inhibit the expression and/or activity of one or more factors of p38 signaling pathway (e.g., p38). The composition includes a small molecule, polynucleotide, a polypeptide, or an antibody or a fragment thereof. Alternatively, or in addition, a composition of the above methods includes a morpholino antisense oligonucleotide, microRNA (miRNA), short hairpin RNA (shRNA), or short interfering RNA (siRNA).

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecule inhibitors can be synthetically engineered to consist of a fragment, or small portion, or a longer amino acid chain to fill a binding pocket of an enzyme. A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

Example commercially available small molecule inhibitors of p38 include: SB 203580 (available from Selleck-Chem, ApexBio, CellSignal, InVivoGen, StemCell); SB 202190 (available from SelleckChem, ApexBio, EMD Millipore, Sigma-Aldrich); SB 239063 (available from Tocris, Sigma-Aldrich, Enzo, Santa Cruz) SB 220025: Sigma-Aldrich, Enzo); SB 242235 (available from Adipogen ApexBio, MedKoo); BIRB-796 (available from Selleck-Chem, ApexBio, LCLabs): VX-702 (available from SelleckChem, ApexBio, Tocris); VX-745 (available from SelleckChem, ApexBio, Tocris); AMG-548 (available from ApexBio, Tocris, Sigma-Aldrich); ARRY-797 (available from ActiveBiochem); PH 797804 (available from Selleck-Chem, ApexBio, Santa Cruz); ARRY-614 (available from ActiveBiochem); SB 681323; GW 856553 (available from MedKoo, MedChemExpress, SelleckChem, Abmole); SCIO-469 (available from Tocris, Santa Cruz, Axon Medchem); BMS 582949 (available from AdooQ); RO 4402257 (available from TRC-Canada, Santa Cruz); and RDP-58; CNI-1493 (available from MedKoo).

The above list is not meant to be limiting of p38 inhibitors. P38 inhibitors of the present invention may be selective for p38, with binding preference for p38 over other MAP kinases.

| 15 | 16 |
|---|---|
| SB203580 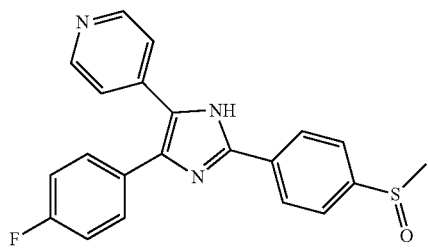 | SB202190 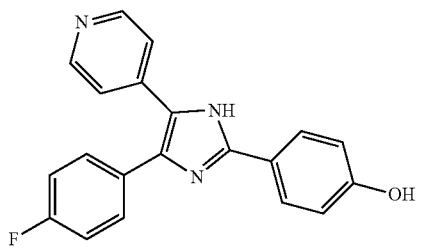 |
| SB239063 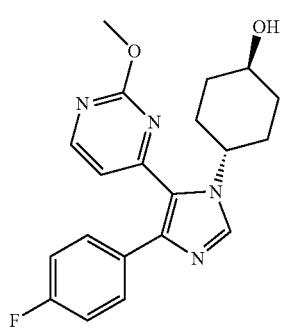 | SB220025 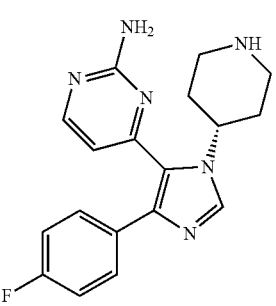 |
| SB242235 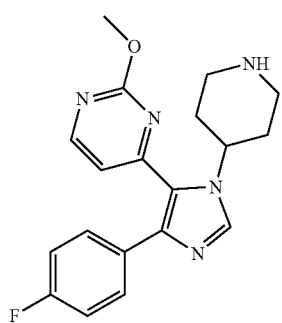 | BIRB-796 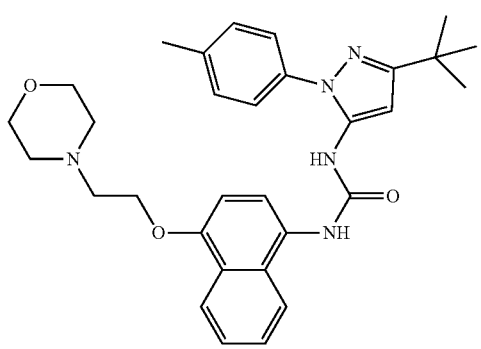 |
| VX-702 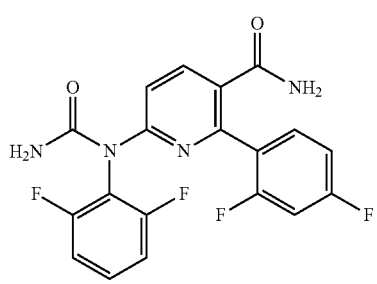 | VX-745 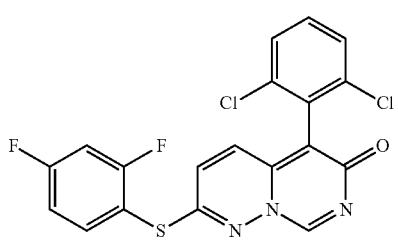 |
| AMG-548 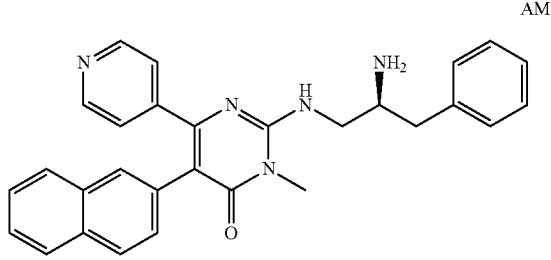 | ARRY-797 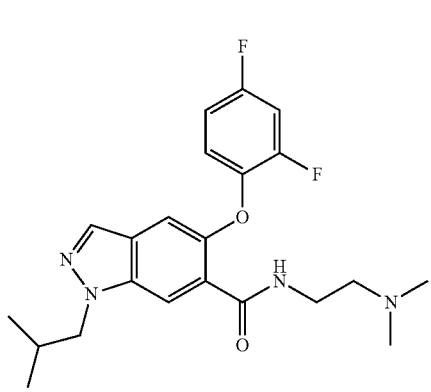 |

-continued
PH797804
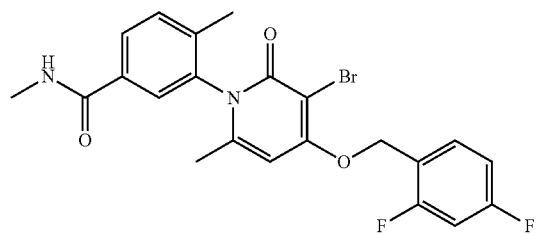
ARRY-614
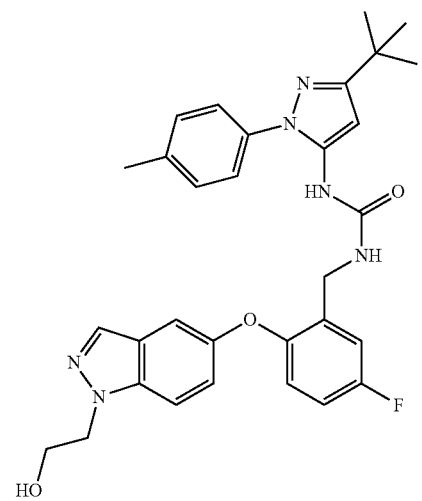
SB 681323
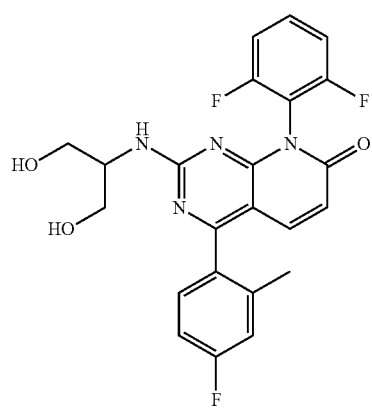
GW 856553
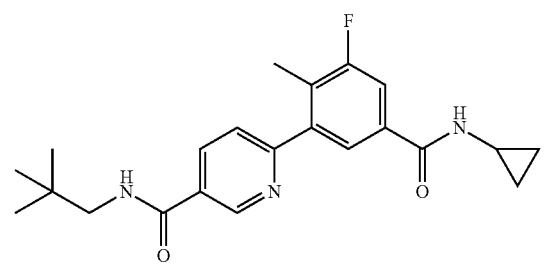
SCIO 469
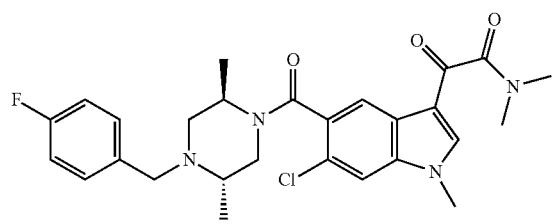
BMS 582949
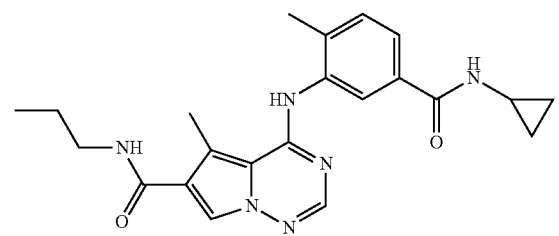
RO 4402257
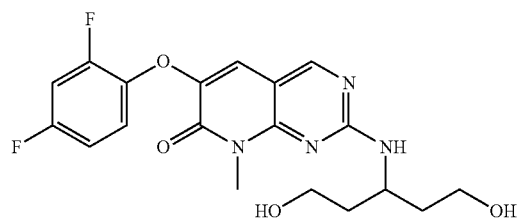

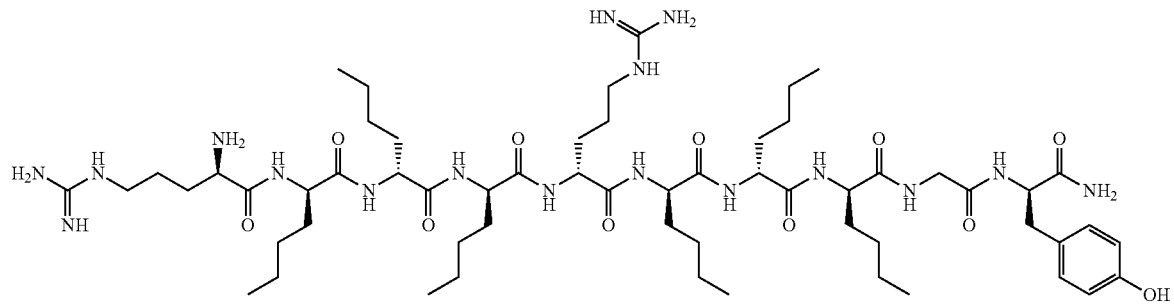
RDP-58
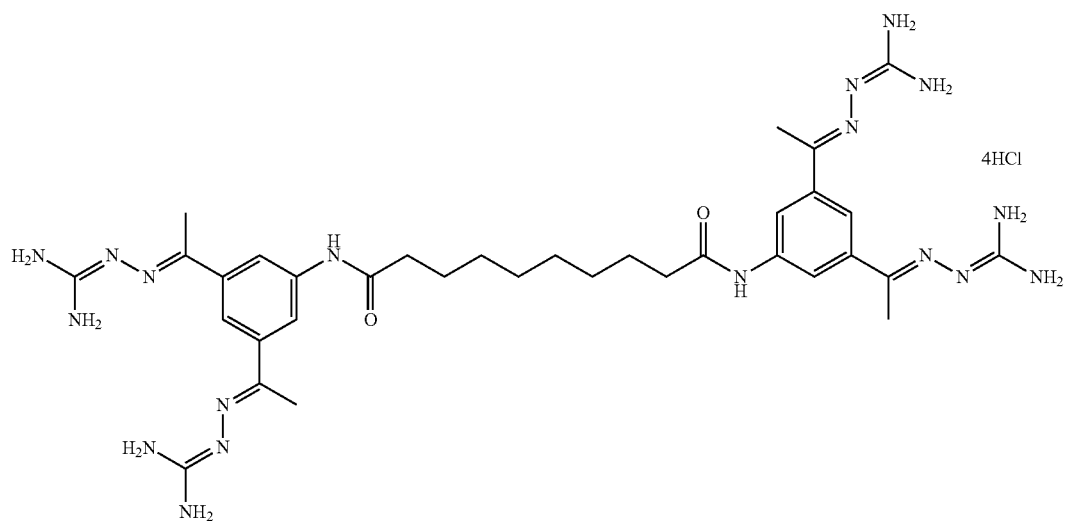
CNI-1493
In preferred embodiments, small molecule inhibitors of p38 include, but are not limited to: p38/SAPK2 (SB202190) (EMD Millipore, cat #19-134: 4-(4-Fluorophenyl)-2-(4-hydroxyphenyl)-5-(4-pyridyl)1H-imidazole).
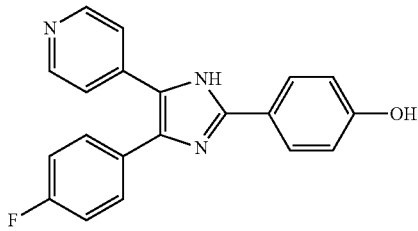
SB202190
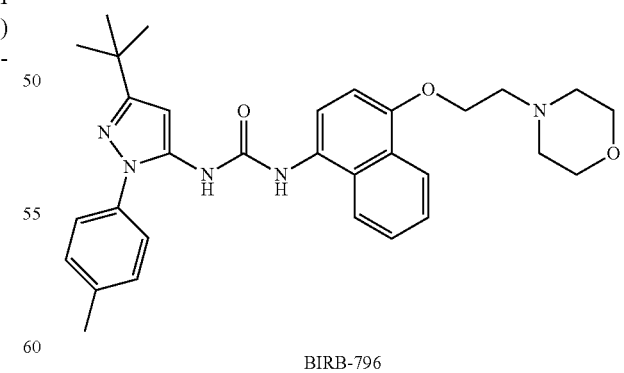
BIRB-796
p38 MAPK Inh X, BIRB-796 (Doramapimod) (EMD Millipore: cat #506172).
SB239063 (trans-1-(4-Hydroxycyclohexyl)-4-(4-fluorophenyl)-5-(2-methoxypyridimidin-4-yl)imidazole) (EMD Millipore: cat #559404).

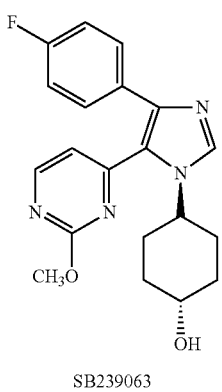

SB239063

SB203580 (4-(4'-Fluorophenyl)-2-(4'-methylsulfinylphenyl)-5-(4'-pyridyl)-imidazole) (EMD Millipore: cat #559398).

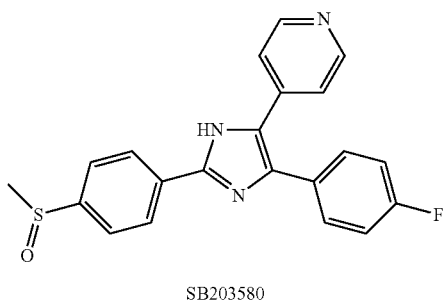 [SMILES: CS(=O)c1ccc(-c2nc(-c3ccc(F)cc3)c(-c3ccncc3)[nH]2)cc1]

SB203580

In embodiments, the inhibitor compound comprises the following formula:

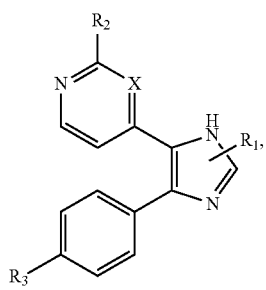

Formula (I)

wherein

R1 is aryl, arylalkyl, heteroaryl, heterocyclic, or carbocyclic, which may be optionally substituted with alkyl, OH, SOR, SO2R, OR, NHR, N(R)2, acetyl, carboxyl where R is alkyl, X is C or N, R2 is hydrogen, alkyl, alkoxy, amine, and R3 is halo, haloalkyl, CN, nitro or sulfonyl.

In some embodiments, R1 is phenyl, hexyl, piperidyl, or pyridyl.

In some embodiments, R3 is methoxy or NH2.

In some embodiments, R3 is F.

Preferably, inhibitors are selective for p38 MAP kinase. Inhibitors may include an antibody or fragment thereof. The anti-p38 antibodies can be intact immunoglobulin molecules such as polyclonal or monoclonal antibodies. Alternatively, the anti-p38 antibodies are antigen-binding fragments including, but not limited to, Fab, F(ab'), F(ab')2, Fv, dAb, Fd, complementarity determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to p38 or a fragment thereof.

Therapeutic Methods

The p38 selective inhibitors are administered in a dose effective to prevent or reverse the development of scar tissue but not to impede beneficial wound healing. Provided herein is a method of treating, reducing or reversing fibrosis of a bodily tissue, by administering to the local affected tissue a compound or a composition described herein, thereby treating, reducing or reversing fibrosis. The compound or the composition as disclosed above may include an inhibitor of p38 or an inhibitor of one factor of p38 signaling pathway. The method may further include identifying a subject with fibrosis in a bodily tissue.

Fibrosis is the formation of excess fibrous connective tissue in an organ or tissue in a reparative or reactive process. Any organ or tissue having fibrosis can be treated by the method described herein. Exemplary bodily tissues includes, but are not limited to, skin, eye, lung, brain, liver, heart, kidney, joint (e.g., knee, shoulder), intestine, hands, fingers, and bone marrow.

The terms "treating" and "treatment" as used herein refer to the administration of an agent or formulation to a clinically symptomatic individual afflicted with an adverse condition, disorder, or disease, e.g., conical scarring or haze, so as to effect a reduction in severity and/or frequency of symptoms, eliminate the symptoms and/or their underlying cause, and/or facilitate improvement or remediation of damage.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

An effective dose or amount, and any possible effects on the timing of administration of the formulation, may need to be identified for any particular formulation of the present invention. This may be accomplished by routine experiment as described herein. The effectiveness of any formulation and method of treatment or prevention may be assessed by administering the formulation and assessing the effect of the administration by measuring one or more indices associated with the efficacy of the active agent and with the degree of comfort to the patient, as described herein, and comparing the post-treatment values of these indices to the values of the same indices prior to treatment or by comparing the post-treatment values of these indices to the values of the same indices using a different formulation.

The precise time of administration and amount of any particular formulation that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

The combined use of several active agents formulated into the compositions of the present invention may reduce the required dosage for any individual component because the onset and duration of effect of the different components may be complimentary. In such combined therapy, the different active agents may be delivered together or separately, and simultaneously or at different times within the day.

The invention provides a method for treating the corneal endothelium and stroma by administering to the eye of a subject in need thereof an ophthalmic formulation comprising an effective amount of one or more p38 inhibitors. In certain embodiments, the concentration of p38 inhibitors may be from 0.10% to 5.0% (w/v), preferably from 0.10% to 2.0%. For treatment of corneal scarring, the inhibitors are formulated with excipients that penetrate the corneal epithelium, thereby gaining access to the corneal endothelium and stroma.

The pH of the formulation is between 5.5 and 7.5. For example, the pH of the formulation is about 7.4. The formulation is in the form of a single dose unit or in the form of a multi-dose system. A single dose unit may be administered within for example, 6 hours, 12 hours, 1 day, 2 days, 3 days, 4 days, 5 days, 6 days, or a week following injury or insult or even weeks, months, years in the case of reversal of scarring. In some embodiments, multiple dosages may be administered over the same time frame.

Suitable forms of the composition include a solution, solid, a paste, an ointment, a gel, a liquid, an aerosol, a mist, a polymer, a film, an emulsion, or a suspension. In some cases, the composition is incorporated into or coated onto a contact lens. For example, the composition is a depot preparation, or a sustained-release formulation. For treatment, reduction, or reversal of corneal scarring, the formulation is preferably a lipid-based formulation. Alternatively, it is an aqueous formulation. The term "aqueous" typically denotes an aqueous composition wherein the carrier is to an extent of >50%, more preferably >75% and in particular >90% by weight water.

In some cases, the method further comprises the administration of a second therapeutic agent. For example, therapeutic agents suitable for treatment of an ocular surface disease include corticosteroids, cyclosporine, or any other appropriate therapeutic agent including agents that target pathogenic cytokines in ocular surface disease such as those that target interleukin-1 (IL-1) or interleukin-17 (IL-17). Agents that target or inhibit interleukin-1 (IL-1) can inhibit or decrease IL-1α or IL-1β expression or activity. For example, agents that target or inhibit IL-1 include, but are not limited to, recombinant and/or soluble IL-1 receptor α or IL-1 receptor β, IL-1α, IL-1β, IL-1Rα, or IL-1Rβ monoclonal antibodies, and small molecule antagonists and/or inverse agonists. An example of an IL-1 receptor antagonist is Anakinra/Kineret (Amgen). Examples of agents that target or inhibit IL-17 include, but are not limited to, recombinant and/or soluble IL-17 receptors, IL-17 or IL-17 receptor monoclonal antibodies, and small molecule antagonists and/or inverse agonists. Examples of commercially available agents that target IL-17 include, but are not limited to Ixekizumab (Eli Lilly and Co.), thymoquinone (Novus Biologicals, Catalog No. NBP2-26241) and plumbagin (Novus Biologicals, Catalog No. NBP2-26242).

The composition comprising the p38 inhibitor is administered at a frequency that affords optimal effectiveness. For example, the composition comprising the p38 inhibitor is administered every 72 hours, every 48 hours, every 24 hours, every 12 hours, every 6 hours, every 3 hours, every 1 hour, or any other appropriate interval. The composition comprising the p38 inhibitor is administered for 1 day, 2 days, 3 days, 4 days, 7 days, 14 days, 30 days, 60 days, 90 days, or 120 days. Alternatively, the composition comprising the p38 inhibitor is administered for long-term use, i.e., more than 120 days, more than 150 days, more than 180 days, more than 210 days, more than 240 days, more than 270 days, more than 300 days, more than 330 days or more than 360 days.

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Optionally, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In a preferred embodiment, a p38 inhibitor of the present invention is not deliverable by a viral or non-viral vector. Delivery to the cornea is challenging given the high propensity for washout from the local tissue. Additionally, compounds of the invention when used to treat or prevent dermal scarring, vector administration is contraindicated due to the larger delivery areas required and complication of uniform delivery across an entire wound area. Compositions of the invention act to block smooth muscle actin (SMA) expression reducing the generation of SMA by myofibroblasts which create scarring. This occurs without inhibiting the production of extracellular matrix, thusly preventing scar tissue formation but not wound healing. Furthermore, evidence is shown that compositions of the present invention may reprogram existing fibroblasts in situ to dedifferentiate myofibroblasts, effectively reducing existing scarring.

The compositions are preferably selective for p38 kinase. The compositions are capable of permeating the corneal epithelium and particularly impacting the corneal stroma. The mechanism of action of the compositions of the present invention is independent of the SMAD pathway.

The form of a p38 inhibitory composition is a solid, a paste, an ointment, a gel, a liquid, an aerosol, a mist, a polymer, a film, an emulsion, or a suspension. The composition is administered topically. In a preferred embodiment, the above methods do not include systemic administration or substantial dissemination to non-ocular tissue when treatment or prevention of corneal haze or scarring and skin scaring is desired. In an additionally preferred embodiment, compositions of the present invention comprising p38 inhibitors are administered concurrently with corneal surgery such as photo refractive keratectomy (PRK) or LASIK surgery, and skin wound from surgery, cut by accident, trauma and burnt. For example, compositions of the invention are administered topically to the eye immediately following injury to the cornea and skin, such as surgery or accidental injury.

Compositions of the invention may be administered prior to, concurrent with, or 1 minute, 2 minutes, 5 minutes after injury, 10 minutes after injury, 15 minutes after injury, 20 minutes after injury, 30 minutes after injury, 45 minutes after injury, 1 hour after injury, 2 hours after injury, 3 hours after injury, 4 hours after injury, 8 hours after injury, 12 hours after injury, or 24 hours after injury. Additionally, compositions can be administered following injury once healing has already begun or once healing has occurred. For example, compositions of the invention can be administered 2 days, 3 days, 4 days, 5 days, 6 days, 7 days, 14 days, 21 days after an injury or insult to the cornea or skin where scarring could or has occurred. Additionally, compositions of the present invention can be administered to the site of past corneal injury that has healed to treat and reverse scarring of the cornea or skin.

In certain embodiments of the above methods, the composition further includes a compound selected from the group consisting of a physiological acceptable salt, poloxamer analogs with carbopol, carbopol/HPMC, carbopol-methyl cellulose, a mucolytic agent, carboxymethylcellulose (CMC), hyaluronic acid, cyclodextrin, dimethyl sulfoxide (DMSO) and petroleum. An exemplary mucolytic agent is N-acetyl cysteine. In a preferred embodiment, the composition further includes carboxymethylcellulose (CMC). In some embodiments, standard excipients are utilized, for example DMSO. In some embodiments, following wounding, the stroma swells and imbibes fluids, therefore solution will be taken up readily.

The invention can be further understood by reference to the following examples, which are provided by way of illustration and are not meant to be limiting.

EXAMPLES

Example 1. p38 Inhibitor (SB202190) Blocks TGF-β1-Induced Increases in Smooth Muscle Actin (SMA) Expression The protocol for alpha smooth muscle actin (αSMA) testing in human corneal fibroblasts (HCF) is shown below using treatment with/without p38 inhibitor (SB202190) as an example treatment.
  1. Grow HCF (human corneal fibroblast cells) in 100 mm dishes (×12).
  2. When cells get 60-70% confluent, rinse with PBS for 3 times. Then:
     a. Put serum-free EMEM to starve cells overnight. (9×)
     b. Put serum-free EMEM with 10 uM of p38 inhibitor (SB202190) overnight to pre-treat cells. (3×)
  3. Next day, treat cells as follows and incubate overnight:
     c. 10 ml of serum-free EMEM (3×)
     d. 10 ml of serum-free EMEM with 2 ng/ml of TGF-β1. (3×)
     e. 10 ml of serum-free EMEM with 10 uM of p38 inhibitor (SB202190). (3×)
     f. 10 ml of serum-free EMEM with 10 uM of p38 inhibitor (SB202190) and 2 ng/ml of TGF-β1 into pre-treated dishes (2b). (3×)
  4. Harvest cells by trypsinization and store cells at −80° C.

Samples were lysed with RIPA buffer and western blot analysis was performed, as previously described (Chung E H, IOVS 1999; 40:1952-8) with minor changes. Membranes with separated proteins were probed with anti-αSMA (alpha-smooth muscle actin) and β-Actin (beta-actin) according to the protocol in Example 1. After reaction with corresponding DyLight secondary antibodies, membranes were scanned on Odyssey and software was used to measure the bands (ImageJ, v. 1.5), and the data was analyzed and plotted (Prism 5.0; GraphPad software).

Figure 1:
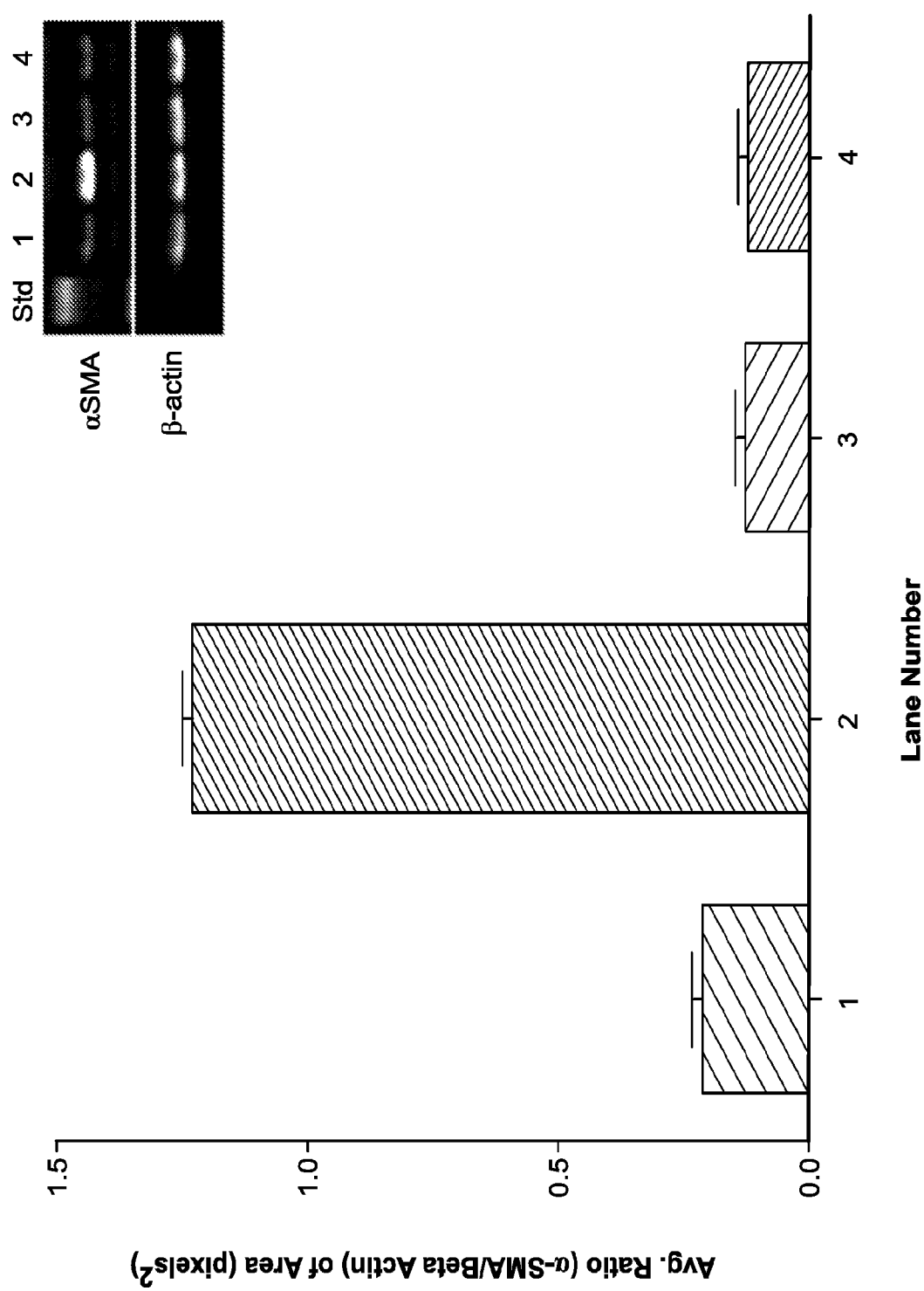
FIG. 1 is an image of a representative western blot of human corneal fibroblasts cultured with 1) Basic Medium (BM: Eagles minimum essential medium) for 48 hours; 2) BM for 24 hours, then BM+TGF-β1 for 24 hours, 3) BM for 24 hours, then BM+p38 inhibitor for 24 hours, and 4) BM+p38 Inhibitor for 24 hours, then BM+p38 inhibitor+TGFβ1. Graph of SMA corrected per lane with internal control (β-actin). Lane 2 is significantly different (p<0.0001) than the other three lanes.

The above protocol was utilized to assay αSMA expression in human corneal and skin fibroblasts under different culture conditions, including in the presence of p38 inhibitor. FIG. 1 shows the image and quantification of a western blot indicating that culturing in the presence of p38 inhibitor (SB202190) inhibits the TGF-β1 induced increase in expression of αSMA as indicated by the ratio of αSMA to β actin (see FIG. 1, column 2 compared to column 4) FIG. 3 shows similar results in human dermal fibroblasts, more important is that the skin myofibroblasts are converted to fibroblasts. In FIG. 3, high levels of αSMA indicate that most dermal fibroblasts in culture were already myofibroblast cells (lane 1). Pre-treatment with p38 inhibitor for 24 hours, demonstrated that αSMA expression was significantly decreased compared with cells in normal culture condition (lane 1) and in the presence of T1 (lane 2). This data indicated that the dermal myofibroblast cells could converted to fibroblast cell in the presence of p38 inhibitor.

FIG. 2A through FIG. 2D shows immunofluorescent images of culture human corneal fibroblasts under varied culture conditions. FIG. 2B indicates that stimulation by TGF-β1 results in increased αSMA staining. This increase in αSMA is mitigated by co-treatment with p38 inhibitor as shown in FIG. 2D.

Example 2. Additional p38 Inhibitors

Figure 4:
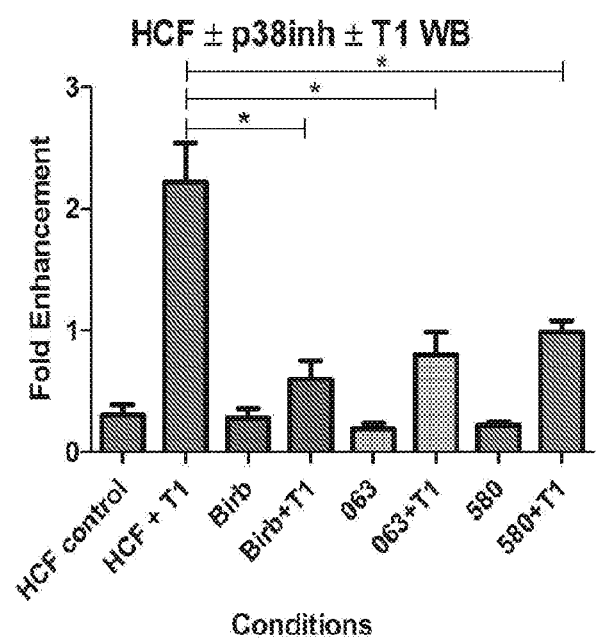
FIG. 4 is a graph depicting analysis of αSMA protein expression in human corneal fibroblasts cultured with 1) Basic Medium (BM: Eagles minimum essential medium) for 48 hours; 2) BM for 24 hours, then BM+TGF-β1 for 24 hours, 3) BM for 24 hours, then BM+Birb-796 for 24 hours, 4) BM+Birb-796 for 24 hours, then BM+Birb-796+TGF-β1 for 24 hours; 5) BM for 24 hours, then BM+SB239063 for 24 hours; 6) BM+SB239063 for 24 hours, then BM+SB239063+TGF-β1 for 24 hours; 7) BM for 24 hours, then BM+SB203580 for 24 hours; and 8) BM+SB203580 for 24 hours, then BM+SB203580+TGF-β1 for 24 hours. Graph of SMA corrected per lane with internal control (β-actin). Lane 2 is significantly different than the other lanes.

Three additional p38 inhibitors shown in Table 1 below were test in HCF. The results shown in FIG. 4 indicate that compared with HCF+TGF-β1, each of these p38 selective inhibitors significantly decreased the αSMA protein expression in HCF in the presence of TGF-β1. The concentrations of these three inhibitors were not optimized and it is believed that with higher concentration of these p38 inhibitors, αSMA expression will be decreased to a greater extent.

TABLE 1

| P38 inhibitors concentration used in the experiments | |
| --- | --- |
| Birb-796 | 10 μM |
| SB239063 | 20 μM |
| SB203580 | 5 uM |

Example 3: Lack of Smad Pathway Involvement in Mechanism

Figure 5:
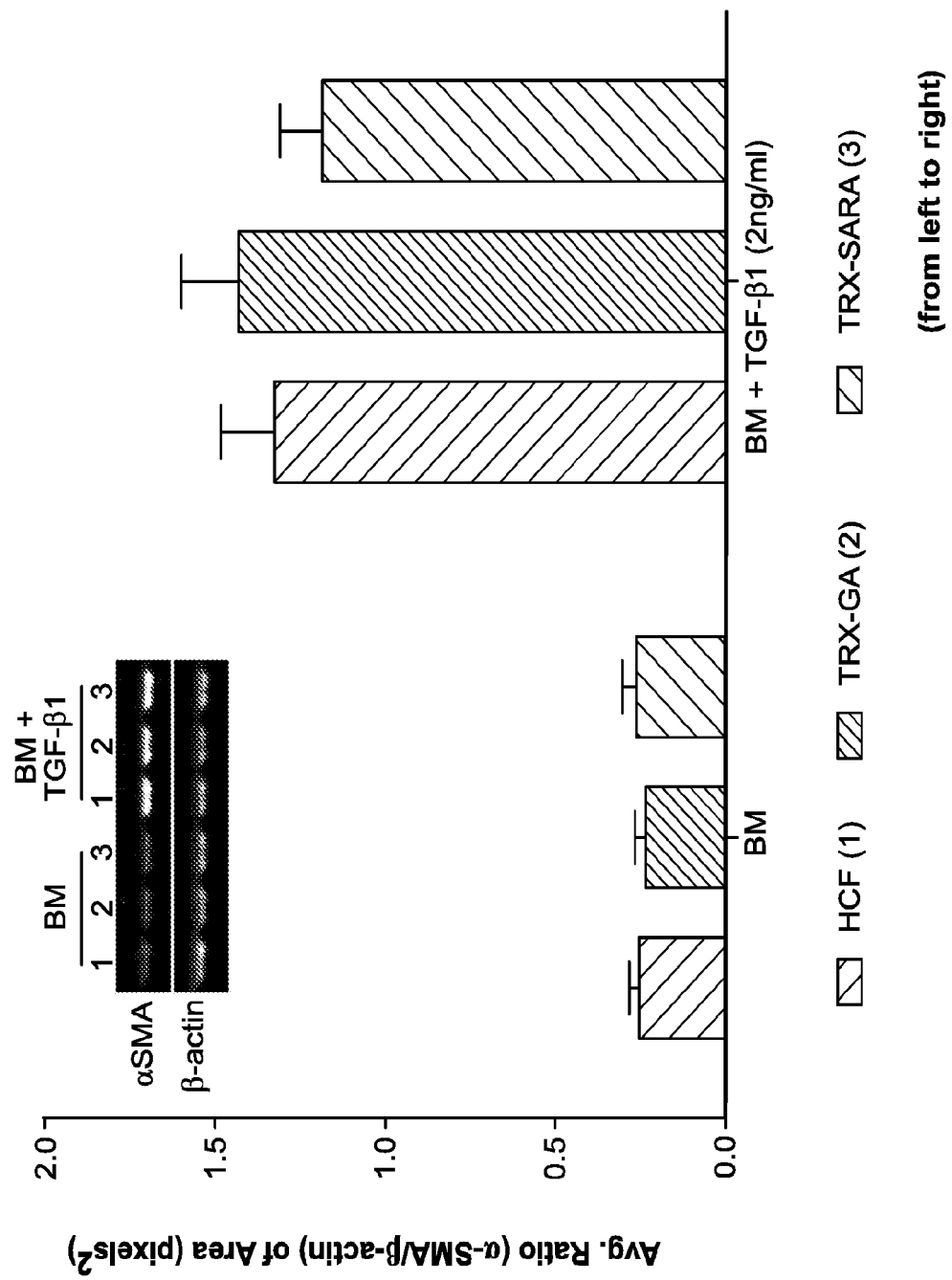
FIG. 5 is a graph showing the analysis of αSMA protein expression in human corneal fibroblasts with or without Trx-SARA. Cells were starved overnight by incubated with BM for 24 hours. Then, Cells cultured with 1) BM for 24 hours; 2) BM+TGF-β1 for 24 hours. Graph of SMA corrected per lane with internal control (β-actin). Lane 6 is not different than lane 4 and 5, two controls.

In FIG. 5, in normal culture condition, all HCF, including normal HCF (control, lane 1), Trx-GA HCF (another control of Trx-SARA, Lane 2), and Trx-SARA HCF in which the Smad signaling pathway was blocked, had low level of αSMA expression. After exposure to T1 for 24 hours, αSMA levels were significantly increased, and no significant difference between, indicating that αSMA is not on Smad pathway.

Figure 6:
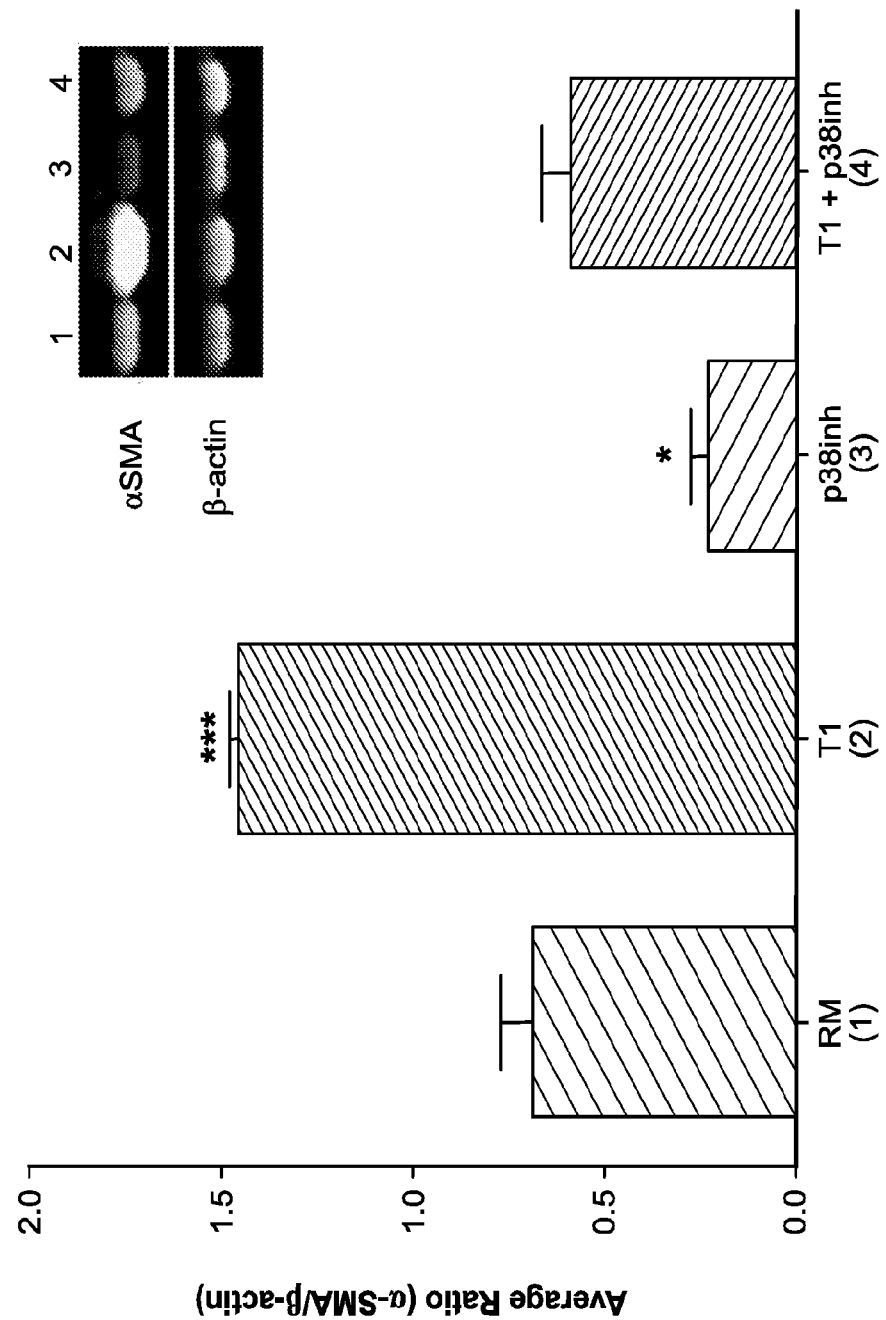
FIG. 6 includes a bar graph and a western blot showing analysis of αSMA expression in human corneal 3-D constructs. Human Corneal Fibroblasts (HCF) were cultured as follows: 1) RM (Regular Medium: Eagle's minimum essential medium+10% FBS for 9 days); 2) T1 (RM for 24 hours, then RM+2 ng/ml of TGF-beta (T1) for 8 days); 3) p38 inhibitor (p38inh) (RM for 24 hours, then RM+10 μM of p38 inhibitor [SB202190] for 8 days); and 4) T1+p38inh (RM+SB202190 for 24 hours, then RM+SB202190+TGF-1 for 8 days). Graph of αSMA corrected per lane with internal control (β-actin). Lane 2 is significantly different (***p<0.001) from the other three lanes. Lane 3 is significantly lower than others (*p<0.05). The western blot is shown in the upper right corner.

Example 4: P38 MAP Kinase Inhibitors for Wound Healing—Inhibition of Fibrosis/Scar Formation Data shown in previous figures were generated using cells in culture. In this experiment, we examined if p38 inhibitor blocked alpha-smooth muscle actin (αSMA) expression in a more physiological 3-dimensional culture system (3-D) (Guo et al., Invest Ophthalmol Vis Sci. 2007 September; 48(9):4050-60; hereby incorporated by reference). The system a cell-based 3-D corneal stromal construct containing human corneal fibroblasts (HCF) and their self-assembled matrix. This art-recognized model mimics stromal development and wound healing. To test this, we cultured human corneal fibroblasts (HCF) in 0.5 mM Vitamin C±2 ng/ml TGF-β1 (T1) and/or 10 μM p38 inhibitor #1 (SB202190) for 9 days. The media was changed every day. After 9 days, the samples were harvested and analyzed for αSMA by western blot (WB). The WB results showed that 3-D data was consistent with the data from single cells. As seen in FIG. 6, after 9 days the αSMA expression in the T1 constructs was significantly upregulated (lane 2, $p<0.001$) compared to control (lane 1); however, in the p38 inhibitor constructs (lane 3), the αSMA expression was significantly decreased ($p<0.05$). Interestingly, when both T1 and p38 inhibitor were present (lane 4), the αSMA expression was significantly lower than T1 (lane 2, $p<0.001$), and decreased as compared with control (lane 1). These results support and confirm the cell culture data and indicate that p38 inhibitor affects the expression of αSMA in the more physiological 3-D culture. The data also indicate that p38 inhibitor(s) inhibit scar formation during corneal wound healing.

Figure 7:
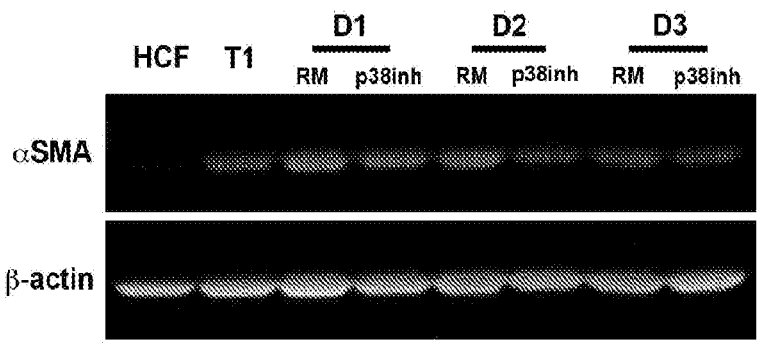
FIGS. 7A and 7B show analysis of αSMA expression in HCF cultured as follows: 1) HCF: RM, 2) T1: RM+T1 (for 3 days), or 3) RM+T1 for 3 days, then RM±p38inh for 1 (D1), 2 (D2), or 3 days (D3). (A) Representative western blot. (B) Graph of αSMA western blot corrected per lane with internal control (β-actin). αSMA expression in T1 is significantly different than in untreated cells (HCF: p<0.0001). On day 2 (D2), αSMA expression in p38inh-treated cells decreased significantly as compared to cells in RM (p<0.05).
Figure 7:
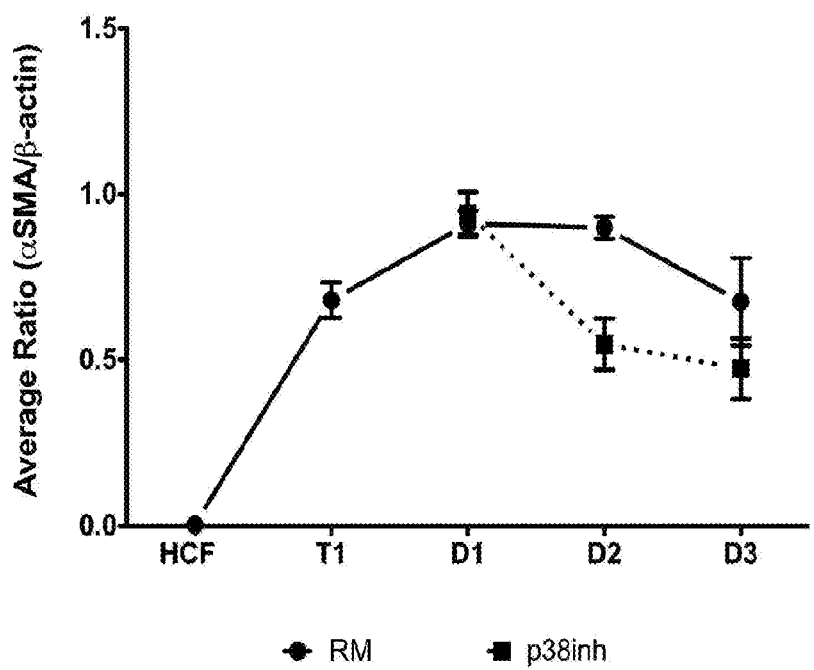

Example 5: Effect of P38 MAP Kinase Inhibitors on Myofibroblasts—Reversal of Fibrosis In this experiment, we examined if p38 inhibitor could not only reduce, but reverse αSMA levels, thus converting myofibroblasts back to their fibroblastic phenotype. To do this, HCF were treated with 2 ng/ml of T1 for 3 days. This allowed for the majority of the HCF to differentiate to their myofibroblastic phenotype with high levels of αSMA expression. After rinsing with PBS three times, these T1-treated cells were split into two groups: 1) regular medium (RM) and 2) p38 inhibitor (p38inh) medium. Media was changed every day. Cells were harvested after 1, 2, or 3 days for αSMA analysis by WB. The WB results showed that αSMA levels in T1 cells (FIG. 7A, lane2) were significantly higher than in the no additives control ($p<0.001$, FIG. 7A, lane 1 [HCF]). The T1 cells then were split into two groups, RM or p38inh, and the appropriate medium was applied. As seen in FIGS. 7A and 7B, on day 1 (D1), αSMA levels in both groups continued to increase, compared to T1 control (lane 2). On day 2 (D2), the αSMA levels in the RM sample leveled out; however, in the p38inh sample, the αSMA levels decreased and were significantly lower than the RM sample at D2 ($p<0.05$). On day 3 (D3), αSMA levels in both media samples decreased. Even though they both decreased, the αSMA level in the p38inh sample continued to be lower than that in the RM sample, which returned to T1 level. These data indicate that although the human corneal myofibroblasts in RM returned to T1 control levels 3 days after the removal of T1 from the culture medium, the presence of p38 inhibitor significantly accelerated the reverse of myofibroblasts to fibroblasts (D2). This data (using the 3-D system described above) also agrees with and confirms the results from human skin fibroblasts in culture.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A method of reversing existing fibrosis of corneal or dermal tissue, comprising:
   administering to the corneal or dermal tissue a composition comprising an inhibitor of p38 MAP kinase,
   thereby reversing existing fibrosis,
   wherein said inhibitor comprises

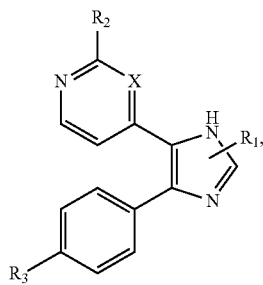

Formula (I)

wherein
   $R_1$ is aryl, arylalkyl, heteroaryl, heterocyclic, or carbocyclic, which may be optionally substituted with alkyl, OH, SOR, $SO_2R$, OR, NHR, $N(R)_2$, acetyl, carboxyl where R is alkyl,
   X is C or N,
   $R_2$ is hydrogen, alkyl, alkoxy, amine, and
   $R_3$ is halo, haloalkyl, CN, nitro or sulfonyl.

2. The method of claim 1, wherein said inhibitor is not an inhibitor of SMAD proteins.

3. The method of claim 1, wherein the inhibitor is selected from the group consisting of SB202190, SB 203580, SB 239063, SB 220025, and SB 242235.

4. The method of claim 1, wherein the inhibitor is selected from the group consisting of SB202190, SB239063, and SB203580.

5. The method of claim 1, wherein the composition is administered following injury to the corneal or dermal tissue.

6. The method of claim 5, wherein the composition is administered within 24 hours following injury to the corneal or dermal tissue.

7. The method of claim 1, wherein the composition is administered locally in advance of a surgical procedure.

8. The method of claim 1, wherein the composition comprises an aqueous solution.

9. The method of claim 1, wherein the composition comprises an eye drop, a cream, or an ointment.

10. The method of claim 1, wherein the composition is administered for 24 hours following injury.

11. The method of claim 1, wherein said tissue comprises corneal tissue.

12. The method of claim 1, wherein said inhibitor is administered locally to the corneal stroma or the corneal endothelium.

13. The method of claim 1, wherein said tissue comprises dermal tissue.

14. The method of claim 1, wherein said inhibitor is administered locally to the dermal tissue.

15. The method claim 1, wherein said inhibitor is administered with an excipient that penetrates epithelial layer of a cornea.

16. The method of claim 15, wherein said excipient comprises a lipid or DMSO.

17. A method of reversing existing fibrosis of the cornea or skin, comprising:
   identifying a subject with existing fibrosis in a skin or corneal tissue;
   locally administering to said skin or corneal tissue a topical composition comprising an inhibitor of p38 MAP kinase.

18. The method of claim 17, wherein the composition comprises an eye drop, a cream, or an ointment.

19. A method of reversing existing fibrosis of a bodily tissue, comprising:
   administering to the local affected tissue a composition comprising an inhibitor of a factor of p38 MAP kinase signaling pathway, thereby reversing existing fibrosis.

20. The method of claim 1, wherein said inhibitor of p38 MAP kinase is administered to the site of an existing scar and reverses fibrosis.

21. A method of reversing existing fibrosis of a bodily tissue, comprising administering to a site of a pre-existing scar an inhibitor of p38 MAP kinase, wherein said inhibitor reverses scarring of cornea or skin.

22. The method of claim 21, wherein the inhibitor comprises SB202190, SB239063, or SB203580.

23. The method of claim 1, wherein the inhibitor of p38 MAP kinase reverses levels of alpha-smooth muscle actin (αSMA).

24. The method of claim 1, wherein the inhibitor of p38 MAP kinase reverses myofibroblasts to fibroblasts in the corneal or dermal tissue.

25. The method of claim 21, wherein the inhibitor of p38 MAP kinase reduces the thickness or stiffness of the pre-existing scar.

26. The method of claim 1, wherein the inhibitor of p38 MAP kinase comprises SB202190.

* * * * *

UNITED STATES PATENT AND TRADEMARK OFFICE
CERTIFICATE OF CORRECTION

| | | |
|---|---|---|
| PATENT NO. | : 11,154,543 B2 | Page 1 of 1 |
| APPLICATION NO. | : 15/768483 | |
| DATED | : October 26, 2021 | |
| INVENTOR(S) | : Xiaoqing Guo and James D. Zieske | |

It is certified that error appears in the above-identified patent and that said Letters Patent is hereby corrected as shown below:

In the Claims

In Column 38, Line 12 (approx.), in Claim 15, after "method" insert -- of --

Signed and Sealed this
Fourteenth Day of June, 2022

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 360
<212> TYPE: PRT
<213> ORGANISM: Homo sapiens

<400> SEQUENCE: 1

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45
```

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
    290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
        355                 360

<210> SEQ ID NO 2
<211> LENGTH: 364
<212> TYPE: PRT
<213> ORGANISM: Homo sapiens

<400> SEQUENCE: 2

Met Ser Gly Pro Arg Ala Gly Phe Tyr Arg Gln Glu Leu Asn Lys Thr
1               5                   10                  15

Val Trp Glu Val Pro Gln Arg Leu Gln Gly Leu Arg Pro Val Gly Ser
            20                  25                  30

Gly Ala Tyr Gly Ser Val Cys Ser Ala Tyr Asp Ala Arg Leu Arg Gln
        35                  40                  45

Lys Val Ala Val Lys Lys Leu Ser Arg Pro Phe Gln Ser Leu Ile His

```
              50                  55                  60
Ala Arg Arg Thr Tyr Arg Glu Leu Arg Leu Leu Lys His Leu Lys His
 65                  70                  75                  80

Glu Asn Val Ile Gly Leu Leu Asp Val Phe Thr Pro Ala Thr Ser Ile
                 85                  90                  95

Glu Asp Phe Ser Glu Val Tyr Leu Val Thr Thr Leu Met Gly Ala Asp
                100                 105                 110

Leu Asn Asn Ile Val Lys Cys Gln Ala Leu Ser Asp Glu His Val Gln
                115                 120                 125

Phe Leu Val Tyr Gln Leu Leu Arg Gly Leu Lys Tyr Ile His Ser Ala
            130                 135                 140

Gly Ile Ile His Arg Asp Leu Lys Pro Ser Asn Val Ala Val Asn Glu
145                 150                 155                 160

Asp Cys Glu Leu Arg Ile Leu Asp Phe Gly Leu Ala Arg Gln Ala Asp
                165                 170                 175

Glu Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
            195                 200                 205

Val Gly Cys Ile Met Ala Glu Leu Leu Gln Gly Lys Ala Leu Phe Pro
210                 215                 220

Gly Ser Asp Tyr Ile Asp Gln Leu Lys Arg Ile Met Glu Val Val Gly
225                 230                 235                 240

Thr Pro Ser Pro Glu Val Leu Ala Lys Ile Ser Ser Glu His Ala Arg
                245                 250                 255

Thr Tyr Ile Gln Ser Leu Pro Pro Met Pro Gln Lys Asp Leu Ser Ser
            260                 265                 270

Ile Phe Arg Gly Ala Asn Pro Leu Ala Ile Asp Leu Leu Gly Arg Met
            275                 280                 285

Leu Val Leu Asp Ser Asp Gln Arg Val Ser Ala Ala Glu Ala Leu Ala
            290                 295                 300

His Ala Tyr Phe Ser Gln Tyr His Asp Pro Glu Asp Glu Pro Glu Ala
305                 310                 315                 320

Glu Pro Tyr Asp Glu Ser Val Glu Ala Lys Glu Arg Thr Leu Glu Glu
                325                 330                 335

Trp Lys Glu Leu Thr Tyr Gln Glu Val Leu Ser Phe Lys Pro Pro Glu
                340                 345                 350

Pro Pro Lys Pro Pro Gly Ser Leu Glu Ile Glu Gln
            355                 360

<210> SEQ ID NO 3
<211> LENGTH: 367
<212> TYPE: PRT
<213> ORGANISM: Homo sapiens

<400> SEQUENCE: 3

Met Ser Ser Pro Pro Ala Arg Ser Gly Phe Tyr Arg Gln Glu Val
 1               5                  10                  15

Thr Lys Thr Ala Trp Glu Val Arg Ala Val Tyr Arg Asp Leu Gln Pro
             20                  25                  30

Val Gly Ser Gly Ala Tyr Gly Ala Val Cys Ser Ala Val Asp Gly Arg
             35                  40                  45

Thr Gly Ala Lys Val Ala Ile Lys Lys Leu Tyr Arg Pro Phe Gln Ser
 50                  55                  60
```

```
Glu Leu Phe Ala Lys Arg Ala Tyr Arg Glu Leu Leu Lys His
 65                  70                  75                  80

Met Arg His Glu Asn Val Ile Gly Leu Leu Asp Val Phe Thr Pro Asp
                 85                  90                  95

Glu Thr Leu Asp Asp Phe Thr Asp Phe Tyr Leu Val Met Pro Phe Met
                100                 105                 110

Gly Thr Asp Leu Gly Lys Leu Met Lys His Glu Lys Leu Gly Glu Asp
                115                 120                 125

Arg Ile Gln Phe Leu Val Tyr Gln Met Leu Lys Gly Leu Arg Tyr Ile
130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
                180                 185                 190

Ala Pro Glu Val Ile Leu Asn Trp Met Arg Tyr Thr Gln Thr Val Asp
                195                 200                 205

Ile Trp Ser Val Gly Cys Ile Met Ala Glu Met Ile Thr Gly Lys Thr
210                 215                 220

Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Gly Lys Lys Asp
                260                 265                 270

Phe Ala Ser Ile Leu Thr Asn Ala Ser Pro Leu Ala Val Asn Leu Leu
                275                 280                 285

Glu Lys Met Leu Val Leu Asp Ala Glu Gln Arg Val Thr Ala Gly Glu
                290                 295                 300

Ala Leu Ala His Pro Tyr Phe Glu Ser Leu His Asp Thr Glu Asp Glu
305                 310                 315                 320

Pro Gln Val Gln Lys Tyr Asp Asp Ser Phe Asp Asp Val Asp Arg Thr
                325                 330                 335

Leu Asp Glu Trp Lys Arg Val Thr Tyr Lys Glu Val Leu Ser Phe Lys
                340                 345                 350

Pro Pro Arg Gln Leu Gly Ala Arg Val Ser Lys Glu Thr Pro Leu
                355                 360                 365

<210> SEQ ID NO 4
<211> LENGTH: 365
<212> TYPE: PRT
<213> ORGANISM: Homo sapiens

<400> SEQUENCE: 4

Met Ser Leu Ile Arg Lys Lys Gly Phe Tyr Lys Gln Asp Val Asn Lys
  1               5                  10                  15

Thr Ala Trp Glu Leu Pro Lys Thr Tyr Val Ser Pro Thr His Val Gly
                 20                  25                  30

Ser Gly Ala Tyr Gly Ser Val Cys Ser Ala Ile Asp Lys Arg Ser Gly
                 35                  40                  45

Glu Lys Val Ala Ile Lys Lys Leu Ser Arg Pro Phe Gln Ser Glu Ile
                 50                  55                  60

Phe Ala Lys Arg Ala Tyr Arg Glu Leu Leu Leu Leu Lys His Met Gln
 65                  70                  75                  80
```

```
His Glu Asn Val Ile Gly Leu Leu Asp Val Phe Thr Pro Ala Ser Ser
                85                  90                  95

Leu Arg Asn Phe Tyr Asp Phe Tyr Leu Val Met Pro Phe Met Gln Thr
            100                 105                 110

Asp Leu Gln Lys Ile Met Gly Met Glu Phe Ser Glu Glu Lys Ile Gln
        115                 120                 125

Tyr Leu Val Tyr Gln Met Leu Lys Gly Leu Lys Tyr Ile His Ser Ala
    130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175

Ala Glu Met Thr Gly Tyr Val Val Thr Arg Trp Tyr Arg Ala Pro Glu
            180                 185                 190

Val Ile Leu Ser Trp Met His Tyr Asn Gln Thr Val Asp Ile Trp Ser
        195                 200                 205

Val Gly Cys Ile Met Ala Glu Met Leu Thr Gly Lys Thr Leu Phe Lys
    210                 215                 220

Gly Lys Asp Tyr Leu Asp Gln Leu Thr Gln Ile Leu Lys Val Thr Gly
225                 230                 235                 240

Val Pro Gly Thr Glu Phe Val Gln Lys Leu Asn Asp Lys Ala Ala Lys
                245                 250                 255

Ser Tyr Ile Gln Ser Leu Pro Gln Thr Pro Arg Lys Asp Phe Thr Gln
            260                 265                 270

Leu Phe Pro Arg Ala Ser Pro Gln Ala Ala Asp Leu Leu Glu Lys Met
        275                 280                 285

Leu Glu Leu Asp Val Asp Lys Arg Leu Thr Ala Ala Gln Ala Leu Thr
    290                 295                 300

His Pro Phe Phe Glu Pro Phe Arg Asp Pro Glu Glu Glu Thr Glu Ala
305                 310                 315                 320

Gln Gln Pro Phe Asp Asp Ser Leu Glu His Glu Lys Leu Thr Val Asp
                325                 330                 335

Glu Trp Lys Gln His Ile Tyr Lys Glu Ile Val Asn Phe Ser Pro Ile
            340                 345                 350

Ala Arg Lys Asp Ser Arg Arg Arg Ser Gly Met Lys Leu
        355                 360                 365
```